(12) United States Patent
Ji et al.

(10) Patent No.: US 8,638,759 B2
(45) Date of Patent: Jan. 28, 2014

(54) SERVING CELL SELECTION IN WIRELESS COMMUNICATIONS

(75) Inventors: Tingfang Ji, San Diego, CA (US); Avneesh Agrawal, San Diego, CA (US); Aamod Khandekar, San Diego, CA (US); Alexei Gorokhov, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 802 days.

(21) Appl. No.: 12/362,289

(22) Filed: Jan. 29, 2009

(65) Prior Publication Data

US 2009/0190500 A1 Jul. 30, 2009

Related U.S. Application Data

(60) Provisional application No. 61/024,880, filed on Jan. 30, 2008.

(51) Int. Cl.
*H04W 52/22* (2009.01)

(52) U.S. Cl.
USPC ............................ 370/332; 370/338; 455/455

(58) Field of Classification Search
None
See application file for complete search history.

(56) References Cited

U.S. PATENT DOCUMENTS

| | | | |
|---|---|---|---|
| 5,710,974 A | 1/1998 | Granlund et al. | |
| 5,809,430 A | 9/1998 | D'amico | |
| 6,771,966 B1 * | 8/2004 | Chow | ............................ 455/446 |
| 6,901,254 B2 | 5/2005 | Ahn | |
| 2005/0272432 A1 | 12/2005 | Ji et al. | |
| 2006/0035640 A1 * | 2/2006 | Karaoguz et al. | ............. 455/437 |
| 2007/0091864 A1 * | 4/2007 | Honjo et al. | ................... 370/338 |
| 2007/0121758 A1 * | 5/2007 | Sindhushayana et al. | ..... 375/297 |
| 2008/0043709 A1 * | 2/2008 | Zhou et al. | ..................... 370/348 |
| 2008/0130582 A1 | 6/2008 | Lee et al. | |
| 2010/0260139 A1 * | 10/2010 | Backstrom et al. | ........... 370/331 |

FOREIGN PATENT DOCUMENTS

| | | |
|---|---|---|
| CN | 1640169 A | 7/2005 |
| CN | 1949919 A | 4/2007 |
| GB | 2337415 A | 11/1999 |
| JP | 11505385 T | 5/1999 |
| JP | 2002515714 A | 5/2002 |
| JP | 2002199430 A | 7/2002 |
| JP | 2003500909 | 1/2003 |

(Continued)

OTHER PUBLICATIONS

International Search Report/Written Opinion—PCT/US09/032586—International Search Authority EPO—May 13, 2009.

(Continued)

*Primary Examiner* — Jianye Wu
(74) *Attorney, Agent, or Firm* — Charles E. Eggers

(57) ABSTRACT

Systems and methodologies are described that facilitate selecting and/or reselecting one or more access points, related cells, or carriers based at least in part on calculating an energy efficiency related to the access points. In particular, the energy efficiency can be based at least in part on an estimated pathloss and/or a level of interference related to communicating with the access points. Moreover, load parameters related to the access point can be received and evaluated in selecting and/or reselecting the access point. Thus, access points can be selected or reselected based on parameters other than forward link transmit power. In addition, pathloss and/or interference levels can be weighed based on access point type to prevent macrocell overloading.

32 Claims, 10 Drawing Sheets

(56) References Cited

FOREIGN PATENT DOCUMENTS

| | | |
|---|---|---|
| JP | 2005229417 A | 8/2005 |
| JP | 2006520172 A | 8/2006 |
| JP | 2007180729 A | 7/2007 |
| KR | 20050075567 A | 7/2005 |
| KR | 20070121947 A | 12/2007 |
| RU | 2113772 C1 | 6/1998 |
| TW | 200637405 | 10/2006 |
| WO | WO96037083 | 11/1996 |
| WO | 9959366 A1 | 11/1999 |
| WO | WO0070897 | 11/2000 |
| WO | WO2004082154 A2 | 9/2004 |
| WO | WO2004084450 | 9/2004 |
| WO | WO2006138570 | 12/2006 |

OTHER PUBLICATIONS

Dorot, V., et al., "An Explanatory Dictionary of Modern Computer Terms," 2nd Edition, BHV-Petersburg Publishers, Saint Petersburg, 2001, 'Program Product' on p. 339.

Wang, L.C., et al., "Tier-Selection Algorithms with Multi-Class Traffic in CDMA Hierarchical Cellular Systems" VTC 2003-Spring. The 57th IEEE Semiannual Vehicular Technology Conference, Proceedings, Jeju, Korea, Apr. 22-25, 2003; New York, US, vol. 2, Apr. 2, 2003, pp. 1158-1162, XP010862597.

Taiwan Search Report—TW098103316—TIPO—Jul. 20, 2012.

\* cited by examiner

SERVING CELL SELECTION IN WIRELESS COMMUNICATIONS

CROSS-REFERENCE TO RELATED APPLICATIONS

This application claims the benefit of U.S. Provisional Patent application Ser. No. 61/024,880 entitled "METHOD AND APPARATUS FOR PERFORMING HANDOFF WITH LOAD AND PATHLOSS ADJUSTMENT IN COMMUNICATION SYSTEMS" which was filed Jan. 30, 2008. The entirety of the aforementioned application is herein incorporated by reference.

BACKGROUND

I. Field

The following description relates generally to wireless communications, and more particularly to selecting serving cells in wireless communication networks.

II. Background

Wireless communication systems are widely deployed to provide various types of communication content such as, for example, voice, data, and so on. Typical wireless communication systems may be multiple-access systems capable of supporting communication with multiple users by sharing available system resources (e.g., bandwidth, transmit power, etc.). Examples of such multiple-access systems may include code division multiple access (CDMA) systems, time division multiple access (TDMA) systems, frequency division multiple access (FDMA) systems, orthogonal frequency division multiple access (OFDMA) systems, and the like. Additionally, the systems can conform to specifications such as third generation partnership project (3GPP), 3GPP long term evolution (LTE), ultra mobile broadband (UMB), etc.

Generally, wireless multiple-access communication systems may simultaneously support communication for multiple mobile devices. Each mobile device may communicate with one or more base stations via transmissions on forward and reverse links. The forward link (or downlink) refers to the communication link from base stations to mobile devices, and the reverse link (or uplink) refers to the communication link from mobile devices to base stations. Further, communications between mobile devices and base stations may be established via single-input single-output (SISO) systems, multiple-input single-output (MISO) systems, multiple-input multiple-output (MIMO) systems, and so forth. In addition, mobile devices can communicate with other mobile devices (and/or base stations with other base stations) in peer-to-peer wireless network configurations.

MIMO systems commonly employ multiple ($N_T$) transmit antennas and multiple ($N_R$) receive antennas for data transmission. The antennas can relate to both base stations and mobile devices, in one example, allowing bi-directional communication between the devices on the wireless network. Mobile devices can initially establish communications with the wireless network via the base stations in a cell or sector serviced by the base station. In heterogeneous deployments, multiple base stations can be available for serving mobile devices in a given cell. For example, over a plurality of contiguous macrocells provided by one or more base stations, femtocells can provide close range service to one or more mobile devices. In this regard, mobile devices can select one or more serving cells for initial service, handoff, and/or the like, which is performed by selecting the serving cell with the highest transmit power. Transmit power, however, may not always be the most desirable indication of an optimal cell for selection and/or reselection.

SUMMARY

The following presents a simplified summary of one or more embodiments to provide a basic understanding of such embodiments. This summary is not an extensive overview of all contemplated embodiments, and is intended to neither identify key or critical elements of all embodiments nor delineate the scope of any or all embodiments. Its sole purpose is to present some concepts of one or more embodiments in a simplified form as a prelude to the more detailed description that is presented later.

In accordance with one or more embodiments and corresponding disclosure thereof, various aspects are described in connection with facilitating selecting serving cells in a wireless network to receive wireless service based on determinations other than or in addition to transmit power in the serving cells. For example, devices selecting serving cells for initial communication, handover, and/or the like, can evaluate cell related parameters such as loading on the cell (which can include number of devices served by the cell, a number of devices typically connected based on historical data, residual capacity of the serving cell, a level of interference in the cell, etc.), pathloss between the cell and device, a level of interference at the cell, and/or the like. Thus, for example, devices can select cells that are closer in proximity, though the cell may have lower transmit power. This can mitigate overall interference on the wireless network. In addition, for example, devices can select cells that are less loaded than a cell having higher transmit power, which can result in increased device performance.

According to related aspects, a method for evaluating an access point for initial communication establishment or reselection thereto is provided. The method can include estimating an energy efficiency related to a pathloss and/or a level of interference associated with an access point. The method further includes comparing the energy efficiency to an energy efficiency of a second access point and establishing communication with the access point based at least in part on comparing the energy efficiency associated with the access point to the energy efficiency of the second access point.

To the accomplishment of the foregoing and related ends, the one or more embodiments comprise the features hereinafter fully described and particularly pointed out in the claims. The following description and the annexed drawings set forth in detail certain illustrative aspects of the one or more embodiments. These aspects are indicative, however, of but a few of the various ways in which the principles of various embodiments may be employed and the described embodiments are intended to include all such aspects and their equivalents.

DETAILED DESCRIPTION

Figure 1:
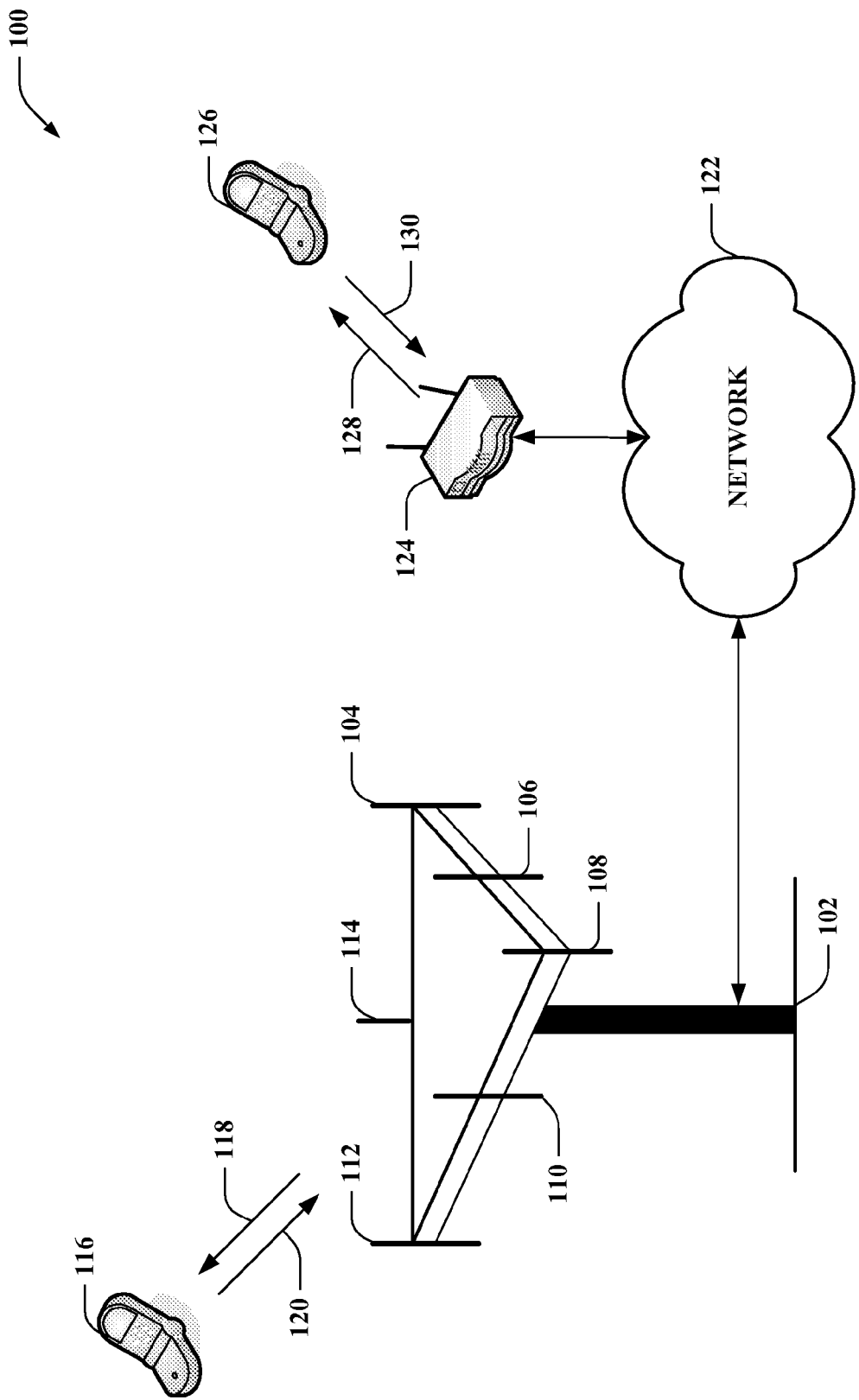
FIG. 1 is an illustration of a wireless communication system in accordance with various aspects set forth herein.

Various embodiments are now described with reference to the drawings, wherein like reference numerals are used to refer to like elements throughout. In the following description, for purposes of explanation, numerous specific details are set forth in-order to provide a thorough understanding of one or more embodiments. It may be evident, however, that such embodiment(s) can be practiced without these specific details. In other instances, well-known structures and devices are shown in block diagram form in-order to facilitate describing one or more embodiments.

As used in this application, the terms "component," "module," "system," and the like are intended to refer to a computer-related entity, either hardware, firmware, a combination of hardware and software, software, or software in execution. For example, a component can be, but is not limited to being, a process running on a processor, a processor, an object, an executable, a thread of execution, a program, and/or a computer. By way of illustration, both an application running on a computing device and the computing device can be a component. One or more components can reside within a process and/or thread of execution and a component can be localized on one computer and/or distributed between two or more computers. In addition, these components can execute from various computer readable media having various data structures stored thereon. The components can communicate by way of local and/or remote processes such as in accordance with a signal having one or more data packets (e.g., data from one component interacting with another component in a local system, distributed system, and/or across a network such as the Internet with other systems by way of the signal).

Furthermore, various embodiments are described herein in connection with a mobile device. A mobile device can also be called a system, subscriber unit, subscriber station, mobile station, mobile, remote station, remote terminal, access terminal, user terminal, terminal, wireless communication device, user agent, user device, or user equipment (UE). A mobile device can be a cellular telephone, a cordless telephone, a Session Initiation Protocol (SIP) phone, a wireless local loop (WLL) station, a personal digital assistant (PDA), a handheld device having wireless connection capability, computing device, or other processing device connected to a wireless modem. Moreover, various embodiments are described herein in connection with a base station. A base station can be utilized for communicating with mobile device(s) and can also be referred to as an access point, Node B, evolved Node B (eNode B or eNB), base transceiver station (BTS) or some other terminology.

Moreover, various aspects or features described herein can be implemented as a method, apparatus, or article of manufacture using standard programming and/or engineering techniques. The term "article of manufacture" as used herein is intended to encompass a computer program accessible from any computer-readable device, carrier, or media. For example, computer-readable media can include but are not limited to magnetic storage devices (e.g., hard disk, floppy disk, magnetic strips, etc.), optical disks (e.g., compact disk (CD), digital versatile disk (DVD), etc.), smart cards, and flash memory devices (e.g., EPROM, card, stick, key drive, etc.). Additionally, various storage media described herein can represent one or more devices and/or other machine-readable media for storing information. The term "machine-readable medium" can include, without being limited to, wireless channels and various other media capable of storing, containing, and/or carrying instruction(s) and/or data.

The techniques described herein may be used for various wireless communication systems such as code division multiple access (CDMA), time division multiple access (TDMA), frequency division multiple access (FDMA), orthogonal frequency division multiple access (OFDMA), single carrier frequency domain multiplexing (SC-FDMA) and other systems. The terms "system" and "network" are often used interchangeably. A CDMA system may implement a radio technology such as Universal Terrestrial Radio Access (UTRA), CDMA2000, etc. UTRA includes Wideband-CDMA (W-CDMA) and other variants of CDMA. CDMA2000 covers IS-2000, IS-95 and IS-856 standards. A TDMA system may implement a radio technology such as Global System for Mobile Communications (GSM). An OFDMA system may implement a radio technology such as Evolved UTRA (E-UTRA), Ultra Mobile Broadband (UMB), IEEE 802.11 (Wi-Fi), IEEE 802.16 (WiMAX), IEEE 802.20, Flash-OFDM, etc. UTRA and E-UTRA are part of Universal Mobile Telecommunication System (UMTS). 3GPP Long Term Evolution (LTE) is an upcoming release that uses E-UTRA, which employs OFDMA on the downlink and SC-FDMA on the uplink. UTRA, E-UTRA, UMTS, LTE and GSM are described in documents from an organization named "3rd Generation Partnership Project" (3GPP). CDMA2000 and UMB are described in documents from an organization named "3rd Generation Partnership Project 2" (3GPP2).

Referring now to FIG. 1, a wireless communication system 100 is illustrated in accordance with various embodiments presented herein. System 100 comprises a base station 102 that can include multiple antenna groups. For example, one antenna group can include antennas 104 and 106, another group can comprise antennas 108 and 110, and an additional group can include antennas 112 and 114. Two antennas are illustrated for each antenna group; however, more or fewer antennas can be utilized for each group. Base station 102 can additionally include a transmitter chain and a receiver chain, each of which can in turn comprise a plurality of components associated with signal transmission and reception (e.g., processors, modulators, multiplexers, demodulators, demultiplexers, antennas, etc.), as will be appreciated by one skilled in the art.

Base station 102 can communicate with one or more mobile devices such as mobile device 116 and mobile device 126; however, it is to be appreciated that base station 102 can communicate with substantially any number of mobile devices similar to mobile devices 116 and 126. As depicted, mobile device 116 is in communication with antennas 112 and 114, where antennas 112 and 114 transmit information to mobile device 116 over a forward link 118 and receive information from mobile device 116 over a reverse link 120. In a frequency division duplex (FDD) system, forward link 118 can utilize a different frequency band than that used by reverse link 120, for example. Further, in a time division duplex (TDD) system, forward link 118 and reverse link 120 can utilize a common frequency.

Each group of antennas and/or the area in which they are designated to communicate can be referred to as a sector or cell of base station 102. For example, antenna groups can be designed to communicate to mobile devices in a sector of the areas covered by base station 102. In communication over forward link 118, the transmitting antennas of base station 102 can utilize beamforming to improve signal-to-noise ratio of forward link 118 for mobile device 116. Also, while base station 102 utilizes beamforming to transmit to mobile device 116 scattered randomly through an associated coverage, mobile devices in neighboring cells can be subject to less interference as compared to a base station transmitting through a single antenna to all its mobile devices. Moreover, though not shown, mobile devices 116 and 126 can communicate directly with one another using a peer-to-peer or ad hoc technology.

In addition, the base station 102 can communicate with a network 122, which can be one or more networks including a wireless service access network (e.g., a 3G network), over a backhaul link connection. The network 122 can store information regarding access parameters related to the mobile device 116 and 126 and other parameters of a wireless access network to provide service to the devices 116 and 126. Furthermore, another base station 124 can be provided to facilitate communicating with the mobile device 126 over forward link 128 and reverse link 130 (similarly to forward link 118 and reverse link 120, as described supra). The base station 124 can be a macrocell base station like base station 102, a femtocell, and/or the like and can provide access to one or more mobile devices 126. In one example, base station 124 can be a femtocell configured in a residence, business, and/or other close range setting (e.g., theme park, stadium, apartment complex, etc.). The base station 124 can also connect to the network 122 utilizing a backhaul link connection, which can be over a broadband Internet connection (T1/T3, digital subscriber line (DSL), cable, etc.), in one example. The network 122 can similarly provide access information for the mobile device 126.

According to an example, mobile devices 116 and 126 can be cellular phones, smart phones, laptops, handheld communication devices, handheld computing devices, satellite radios, global positioning systems, PDAs, and/or any other suitable device for communicating over wireless communication system 100. The mobile devices 116 and 126 can travel over service areas performing cell reselection among disparate base stations and/or femtocells during travel. Disparate, as used herein, can be defined as different, different in kind, distinct, separate, distinct in quality or character, etc. Thus, disparate base stations can be of the same, substantially similar, somewhat different, or completely different technology so long as the base stations provide wireless access to one or more devices. In addition, in one example, the base stations can be of substantially the same technology and/or constructed from the same components and operated by the same or a different wireless access provider. In this regard, the mobile devices 116 and 126 can effectuate continuous wireless service seamless to users of the mobile devices 116 and 126. In one example (not shown), mobile device 126 can have been communicating with the base station 102 similarly to the mobile device 116, and can have moved into a specified range of the base station 124. In this regard, the mobile device 126 can have reselected one or more cells related to the base station 124 to receive more desirable wireless service access. In one example, the base station 124 can be a home access point for the mobile device 126 offering more desirable billing and/or other access options. In another example, the base station 124 can be related to a business or venue offering options or data tailored to the respective business or venue. Thus, mobile device 126 can initially select and/or reselect one or more cells related to the base station 124 to receive such tailored options. In addition, as mobile device 126 moves toward base station 102, it can reselect a cell related thereto.

In traveling over the service area, mobile devices 116 and/or 126 can continually measure various parameters related to available base stations (such as base stations 102 and 124), which can be macrocell base stations, femtocell access points, and/or other access points. The mobile devices 116 and/or 126 can determine when to perform cell reselection based on the measurements. In addition, upon initial connection, the mobile devices 116 and/or 126 can perform similar measurements to select an initial cell for receiving wireless access services. Performing measurements can include, for example, inferring information from measurements such as comparing communication parameters related to each of the base stations 102 and 124. The parameters can be calculated, estimated, or otherwise determined. In one example, the communication parameters can relate to evaluating a transmit power of the base stations 102 and 124, estimating a pathloss related to the base stations 102 and 124, determining a level of interference associated with the base stations 102 and 124, evaluating one or more loading parameters of the base stations 102 and 124 (such as number of devices receiving service, residual capacity, interference in one or more related cells, etc.), and/or the like. It is to be appreciated that pathloss can refer to reduction in power of a signal between a transmitter and a receiver. Thus, parameters other than merely transmit power can be analyzed in evaluating cells for reselection.

According to an example, the mobile device 126 can move into range of base station 124, or initially evaluate surrounding base stations to receive wireless access. The mobile device 126 can receive signals from base station 102 as well as base station 124. Depending on proximity, the signal strength of base station 102 can be greater than that of base station 124. The mobile device 126, however, can be geographically close to base station 124 such that selecting base station 102 for service over base station 124 can provide substantial interference in the area serviced by base station 124. In another example, the base station 102 can be close to loading capacity whereas base station 124 has more resources available to serve the mobile device 126. In these examples, cells available at the base station 102 may not be the most desirable for the mobile device 126. Thus, the mobile device 126 can compare communications parameters related to both of base stations 102 and 124. Comparing communications parameters can include, for example, estimating a respective pathloss for the base stations 102 and 124, determining an interference level related to both base stations 102 and 124, analyzing loading parameters related to the base stations 102 and 124 in evaluating for reselection, initial communication establishment, etc.

Figure 2:
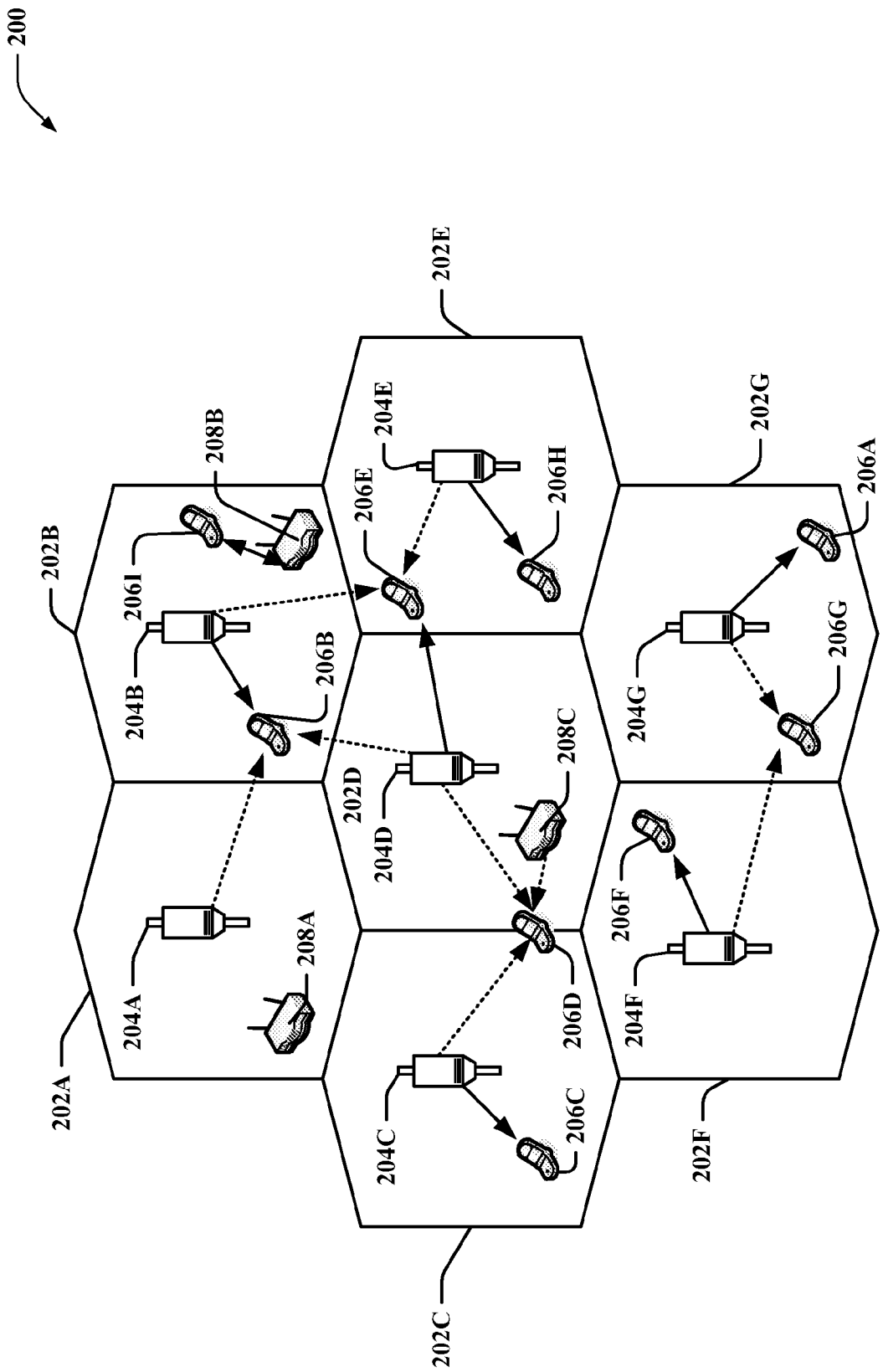
FIG. 2 is an illustration of a heterogeneously deployed wireless communications system in accordance with various aspects set forth herein.

Now referring to FIG. 2, a wireless communication system 200 configured to support a number of mobile devices is illustrated. The system 200 provides communication for multiple cells, such as for example, macrocells 202A-202G, with each cell being serviced by a corresponding access point 204A-204G. As described previously, for instance, the access points 204A-204G related to the macrocells 202A-202G can be macrocell base stations. Mobile devices 206A-206I are shown dispersed at various locations throughout the wireless communication system 200. Each mobile device 206A-206I can communicate with one or more access points 204A-204G on a forward link and/or a reverse link, as described. In addition, access points 208A-208C are shown. These can be smaller scale access points, such as femtocells, relay nodes, wireless access points, mobile access points, etc., offering services related to a particular service location, as described. The mobile devices 206A-206I can additionally communicate with these smaller scale access points 208A-208C to receive offered services. The wireless communication system 200 can provide service over a large geographic region, in one example (e.g., macrocells 202A-202G can cover a few blocks in a neighborhood, and the smaller scale access points 208A-208C can be present in areas such as residences, office buildings, and/or the like as described). In an example, the mobile devices 206A-206I can establish connection with the access points 204A-204G and/or 208A-208C over the air and/or over a backhaul connection.

Additionally, as shown, the mobile devices 206A-206I can travel throughout the system 200 and can reselect cells related to the various access points 204A-204G and/or 208A-208C as it moves through the different macrocells 202A-202G or smaller scale coverage areas. In addition, the mobile devices 206A-206I can perform similar cell selection upon establishing an initial communication to receive wireless access services. For example, mobile device 206D can evaluate surrounding cells 202C and 202D provided by access points 204C and 204D, respectively, as well as a coverage area provided by the smaller scale access point 208C for reselection or initial communication establishment. The mobile device 206D can compare transmit powers of each access point 204C, 204D, and 208C, in one example. In addition, however, the mobile device 206D can estimate a pathloss to each access point 204C, 204D, and 208C, and/or determine a related level of interference to utilize in evaluating the cells. In one example, the pathloss can be estimated by comparing transmit antenna output to receive antenna output or by using other known methods.

Moreover, as described, the mobile device 206D can receive parameters related to load on the access points 204C, 204D, and/or 208C. For example, the parameters can relate to a number of devices currently served by the access points 204C, 204D, 208C, and/or a related cell, a residual capacity thereof related to number of devices, number of resources, and/or the like, a level of interference at the access points 204C, 204D, 208C, and/or related cell, etc. It is to be appreciated that the parameters can be received from the access points 204C, 204D, 208C, and/or other network components. Thus, the load parameters, or one or more combinations of parameters, can be utilized as well to evaluate the surrounding cells for initial selection and/or reselection thereto.

According to the above example, transmit power from the access points 204C and 204D can be stronger than that of the smaller scale access point 208C. The mobile device 206D, however, can be geographically close to the smaller scale access point 208C such that pathloss is lower than with the access points 204C and 204D. This additional consideration of pathloss allows the mobile device 206D to select smaller scale access point 208C for wireless access, which decreases interference the smaller scale access point 208C and other devices would experience if the mobile device 206D was communicating with access point 204C or 204D. Additionally, in this regard, the mobile device 206D can analyze the interference level of the smaller scale access point 208C as compared to the access points 204C and/or 204D within a specified range of allowed interference for smaller scale access points. Thus, the interference for smaller scale access point 208C can be higher than that of the access points 204C and/or 204D, and the mobile device 206D can select/reselect the smaller scale access point 208C where the difference is within the specified range. This prevents overloading of the macrocells 204C and/or 204D where the mobile device 206D is in a geographical proximity to receive service from the smaller scale access point 208C within the specified range of allowed interference.

According to another example, the smaller scale access point 208C can be near loading capacity, and the related loading parameters received by the mobile device 206D can indicate such. The mobile device 206D can analyze the parameters in evaluating the access point 208C such that where the access point 208C is near capacity, the mobile device 206D can select access point 204C and/or 204D for receiving wireless access services, for example. In this regard, using the example above, the smaller scale access point 208C can advertise an effective interference over thermal (IoT) parameter that can be analyzed by the mobile device 206D. The effective IoT can be based on capacity of the access point 208C, for example. Macrocell access points 204C and 204D can advertise a normal IoT parameter, which relates to a level of interference normalized by thermal noise. The mobile device 206D can thus consider the normal IoT of the access points 204C and 204D as compared with the effective IoT parameters of the access point 208C in determining a cell for selection/reselection. In this regard, overloading of the access points 204C and 204D is mitigated as the smaller scale access point 208C parameters are offset as related to loading capacity.

Figure 3:
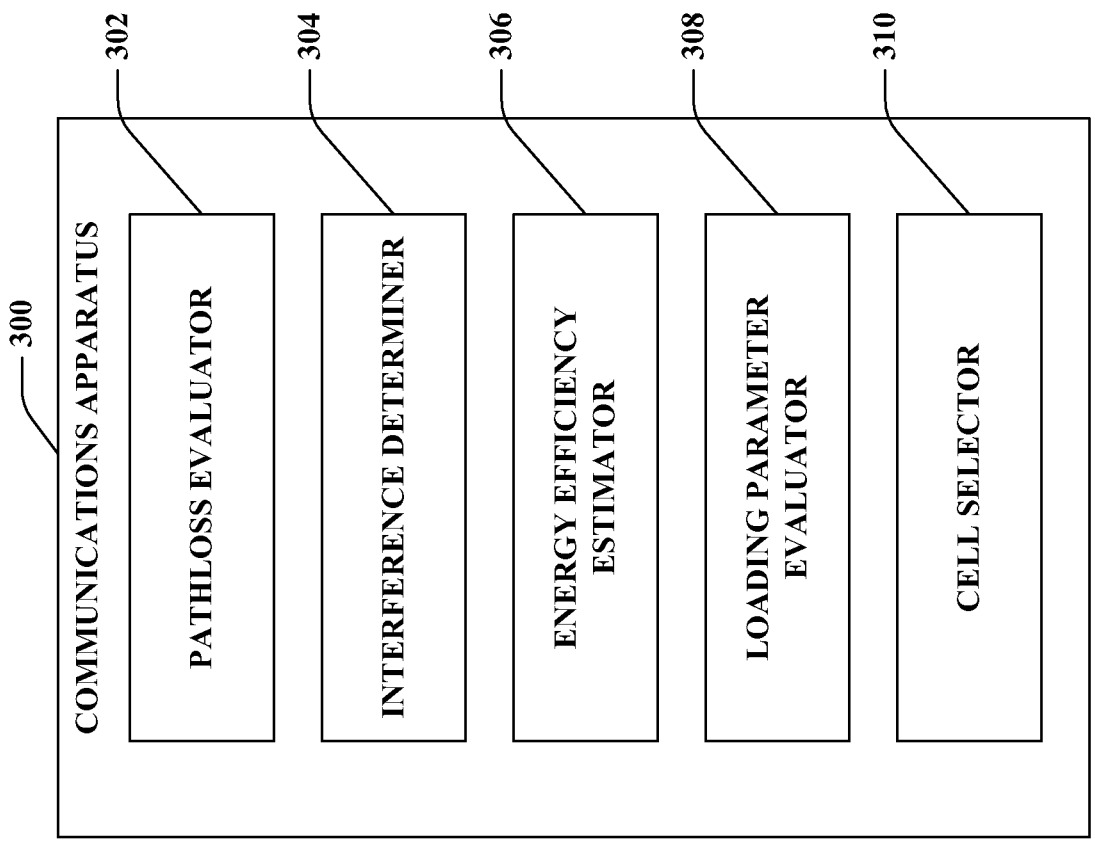
FIG. 3 is an illustration of an example wireless communications system that effectuates determining energy efficiency and/or receiving loading parameters to perform cell selection or reselection.

Turning to FIG. 3, illustrated is a communications apparatus 300 for employment within a wireless communications environment. The communications apparatus 300 can be a base station or a portion thereof, a mobile device or a portion thereof, or substantially any communications apparatus that receives data transmitted in a wireless communications environment. The communications apparatus 300 can include a pathloss evaluator 302 that can receive and analyze pathloss related to one or more disparate communications apparatuses (not shown) or related cells, an interference determiner 304 that can ascertain interference associated with the apparatuses or cells, an energy efficiency estimator 306 that can compute an energy efficiency related to establishing communication with the apparatuses or cells based at least in part on the pathloss and interference, a loading parameter evaluator 308 that can receive one or more loading parameters related to the disparate communications apparatuses or cells, and a cell selector 310 that can request and/or establish communication with one or more of the disparate communications apparatuses or cells based on the pathloss, interference, energy efficiency, and/or loading parameters.

According to an example, the communications apparatus 300 can determine one or more surrounding cells or related apparatuses from which to request connection establishment or cell reselection. The pathloss evaluator 302 can receive pathloss related to communication between the communications apparatus 300 and the one or more surrounding cells or related apparatuses. As described, the pathloss evaluator 302 can estimate the pathloss based on a transmit and receive power and/or utilizing other known prediction techniques. In one example, the pathloss can be estimated using the following formula:

$$h = C_i / \text{EIRP}_i$$

where h is the pathloss, $C_i$ is the signal power from access point i (where i is a positive integer), and $\text{EIRP}_i$ is the equivalent isotropically radiated power (EIRP) related to the access point i. The cell selector 310 can analyze the pathloss from the pathloss evaluator 302 in determining a cell or related apparatus for establishing communications.

In addition, the interference determiner 304 can discern interference related to a plurality of cells or related apparatuses, and the cell selector 310 can additionally or alternatively select or reselect a cell or related apparatus to minimize interference. Moreover, the energy efficiency estimator 306 can calculate an energy efficiency for each of the plurality of cells or related apparatuses, and the cell selector 310 can select/reselect based additionally or alternatively on a minimum energy efficiency ($\min(E_{b,tx})$). The energy efficiency $E_{b,tx}$ for a given cell or related apparatus can be expressed as follows:

$$E_{b,tx} = E_{b,rx}/h = (E_{s,rx}/r)/h = E_{s,rx}/(h \log 2(1+C/I))$$

where r is the spectral efficiency in bits per second (bps)/hertz (Hz), C is the received signal power of the cell or apparatus, I is the received interference power (e.g., determined by the interference determiner 304) of the cell or apparatus, and h is the pathloss (e.g., determined by the pathloss evaluator) as described above. Thus, the energy efficiency estimator 306 can calculate the energy efficiency $E_{b,tx}$ for a given cell or related apparatus using the following formula accounting for interference avoidance at the cells:

$$E_{b,tx} \approx E_{s,rx} \log 2/(hC/I) = \log 2(C/B)/(hC/I) = (\log 2/B)I/h$$

where B is the symbol rate. In another example, the interference determiner 304 can compute interference as total received power minus signal power from a given cell where no interference avoidance is performed related to the given cell. In this regard, the following formula can be utilized by the energy efficiency estimator 306 in determining $E_{b,tx}$ for one or more cells:

$$E_{b,tx} \approx (\log 2/B)(Y-C)/h$$

where Y is the total received power. As described, the cell selector 310 can select/reselect the cell or related apparatus exhibiting the minimum $E_{b,tx}$. Moreover, cells and/or related apparatuses can have different interference levels over different interlaces, in one example. In this regard, the energy efficiency estimator 306 can calculate energy efficiency over the active interlaces, which can be those over which the cells and/or related apparatuses are expected to schedule data transmissions to the communications apparatus 300.

According to another example, the loading parameter evaluator 308 can receive one or more loading parameters related to loading conditions on the cells or related apparatuses. For example, the loading parameters can relate to a capacity and/or usage of a given cell, such as the number of devices the cell can support, the number of devices currently served by the cells, number of devices typically served by the cell (e.g., based on historical data), resources available at the cell, residual capacity of the cell, a fraction or percentage of availability, and the like. In addition, the loading parameter evaluator 308 can compute values from one or more received parameters, such as a percentage of capacity utilized from received capacity and utilization parameters. The cell selector 310 can select/reselect a cell based on the one or more received loading parameters. For example, where the cell selector 310 is receiving service in a current cell, it can compare the one or more loading parameters with one or more disparate loading parameters related to the current cell to determine whether to reselect. Additionally, the cell selector 310 can select/reselect the cell or related apparatus subject to control channel reliability and/or carrier-to-interference ratio (C/I) due to residual error rate.

Figure 4:
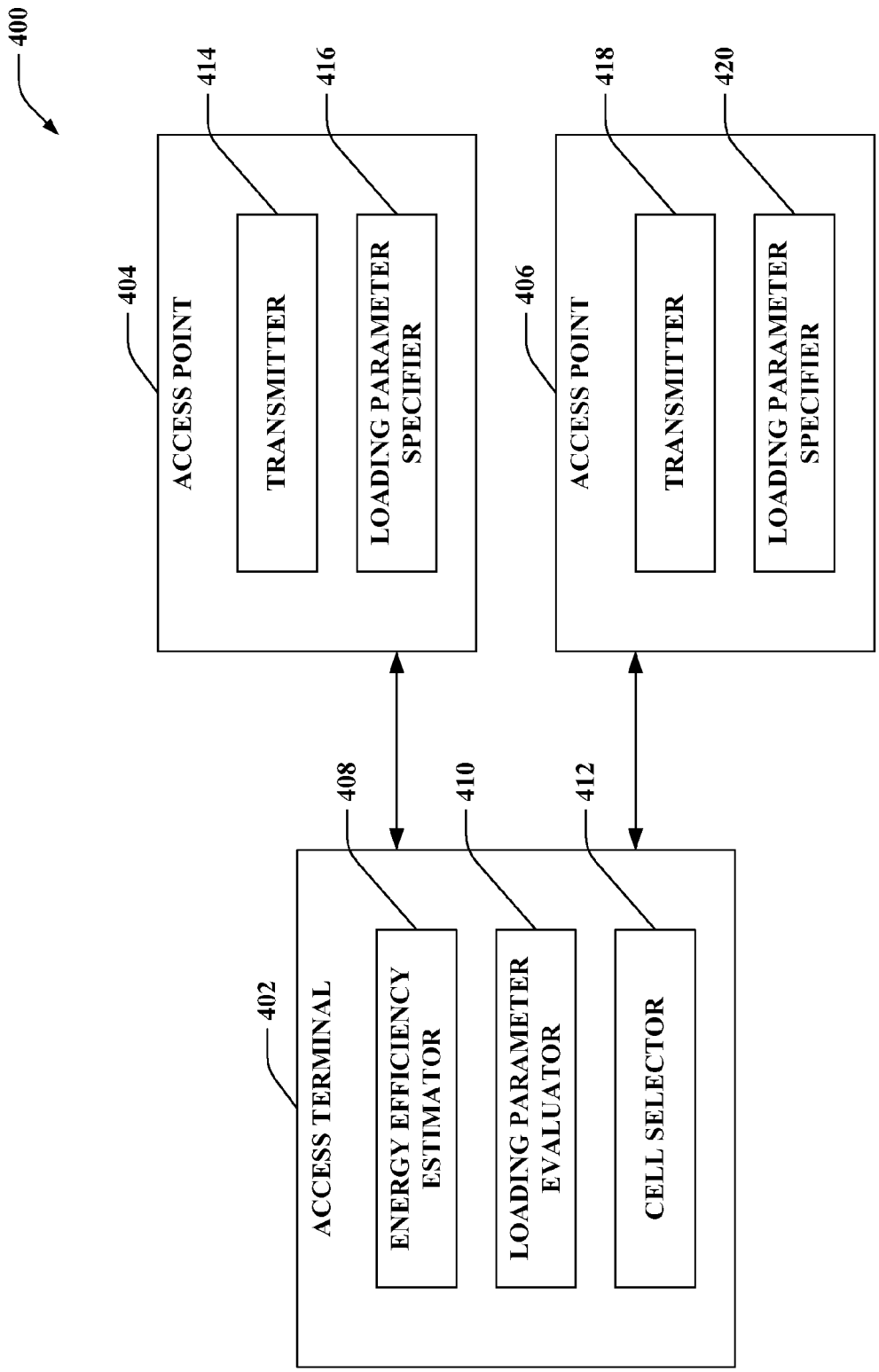
FIG. 4 is an illustration of an example wireless communication system for cell selection/reselection based at least in part on an estimated energy efficiency and/or received load parameters.

Now referring to FIG. 4, illustrated is a wireless communications system 400 that can allow cell selection/reselection based at least in part on energy efficiency and/or load parameters related to multiple access points. The system includes an access terminal 402 and access points 404 and 406, each of which can be a base station, mobile device, or portion thereof, for example. In one example, access terminal 402 can transmit information to access points 404 and/or 406 over a reverse link or uplink channel; further access terminal 402 can receive information from access points 404 and/or 406 over a forward link or downlink channel. Moreover, system 400 can be a MIMO system. Also, the components and functionalities shown and described below in the access terminal 402 can be present in the access points 404 and 406 as well and vice versa, in one example; the configuration depicted excludes these components for ease of explanation.

Access terminal 402 includes an energy efficiency estimator 408 that, as described, can compute an energy efficiency of one or more access points 404 and 406 or related cells from determined pathloss and/or interference measurements, a loading parameter evaluator 410 that can receive one or more loading parameters from the one or more access points 404 and 406, and a cell selector 412 that can initially establish communications with or perform cell reselection to the one or more access points 404 and 406. In addition, the access point 404 can include a transmitter 414 that transmits various signals that can be received by the access terminal 402 and a loading parameter specifier 416 that can provide loading parameters to be transmitted. Similarly, access point 406 also comprises a transmitter 418 and loading parameter specifier 420.

According to an example, the access terminal 402 can be receiving wireless access services from the access point 404. As the access terminal 402 moves around a service area, it can evaluate other access points for cell reselection. Thus, the energy efficiency estimator 408 can calculate energy efficiency related to reselecting to one or more access points 406 as well as that of the current access point 404. The cell selector 412, as described, can determine whether to reselect the access point 406 based at least in part on comparing the energy efficiency calculations. In another example, the loading parameter specifiers 416 and 418 can specify one or more loading parameters related to the respective access point 404 and 406, which can relate to number of devices currently supported, residual capacity, etc., as described, which can be transmitted over respective transmitters 414 and 418. The loading parameter evaluator 410 can analyze the loading parameters, and the cell selector 412 can additionally consider the loading parameters in determining whether to reselect to access point 406, as described.

According to an example, the transmitters 414 and 418 can transmit pilot signals related to respective access points 404 and 406; the energy efficiency estimator 408 can determine an interference level of related to the pilot signals. In addition, the energy efficiency estimator 408 can measure signal strength of the pilot signals, such as an EIRP, and compute pathloss for the access points 404 and 406, as described above. The cell selector 412 can determine whether to reselect to access point 406 based at least in part on the pathloss computations. In one example, where interference levels are similar at access points 404 and 406, the energy efficiency estimator 408 can weigh one interference level higher than the other based on a type of the access points 404 and 406 (e.g., macrocell access point, femtocell or other small coverage area access point, etc.), as described above. Furthermore, the energy efficiency estimator 408 can evaluate different provided interference calculations based on a type of the access points 404 and 406.

In one example, interference at access point 404, as measured by the energy efficiency estimator 408, can be a function of interference at access point 406. As described, the interference can be based on whether or not interference avoidance is performed at the access points 404 and 406. In addition, interference utilized by the energy efficiency estimator 408 can be IoT. In this case, the following formula can be used, in one example:

$$E_{b,tx} \approx (\log 2/B)I/h = \log 2(I/B)/h = \log 2(\text{IoT} \times N0)/h$$

As described, the IoT utilized can be based on a type of the access points 404 and 406. In one example, the IoT can be received from the access points 404 and 406. For example, where the access point is a smaller coverage area access point, an effective IoT can be received and utilized by the energy efficiency estimator 408. Where the access point is a macrocell or large coverage area access point, a normal IoT can be received and utilized by the energy efficiency estimator, as described. It is to be appreciated that the cell selector 412 can use the foregoing in determining whether to initially connect to the access point 404 and 406, in another example. According to yet another example, the access terminal 402 can have a multicarrier receiver such that it can communicate with disparate carriers of access points 404 and/or 406. Thus, the loading parameter specifiers 416 and/or 420 can specify loading parameters on individual carriers of the respective access points 404 and 406. The loading parameter evaluator 410 can analyze the loading parameters to determine which carrier(s) to utilize, and the cell selector 412 can select appropriate carrier(s) based on the analysis.

Figure 5:
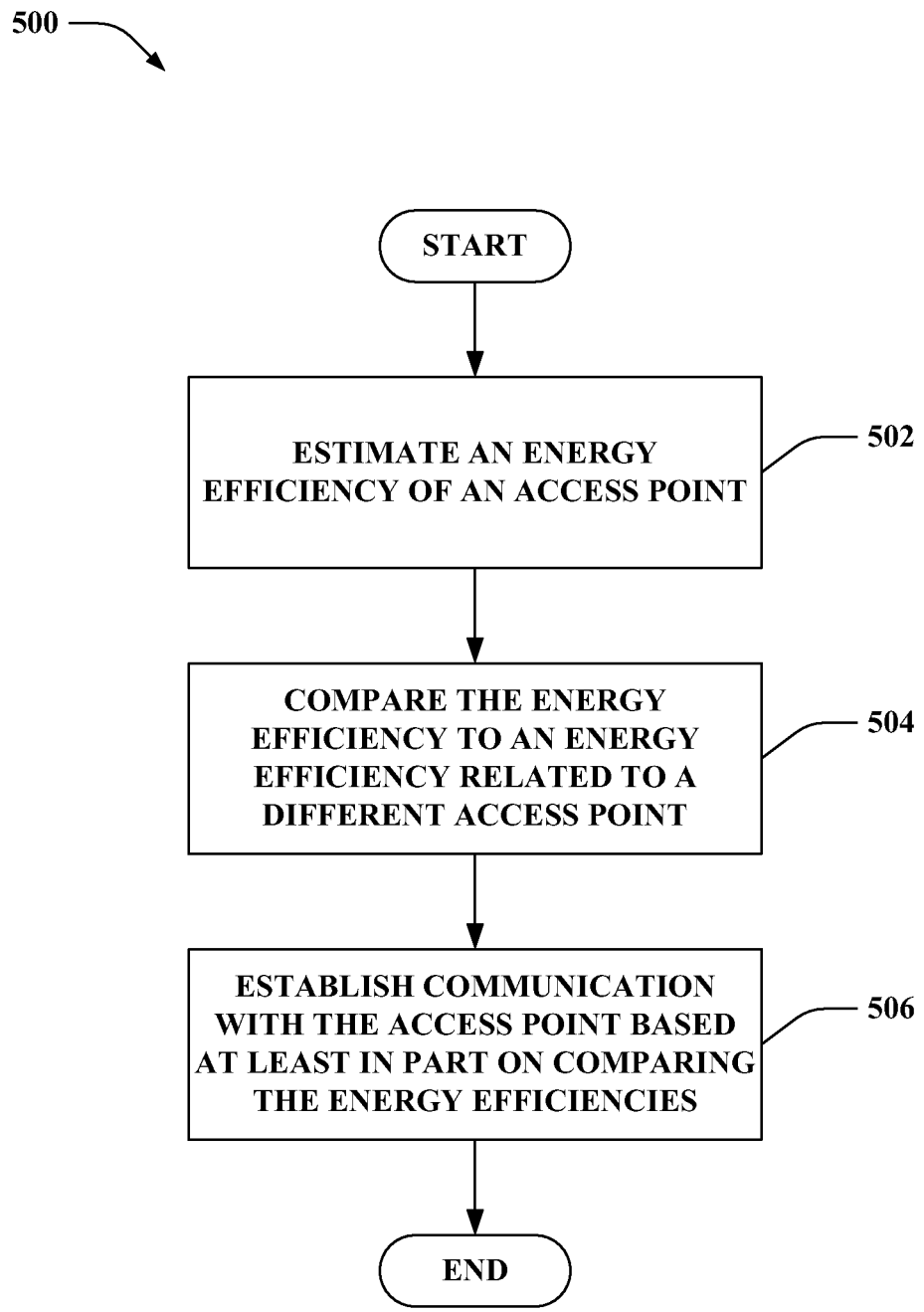
FIG. 5 is an illustration of an example methodology that facilitates cell selection/reselection based on estimating an energy efficiency.
Figure 6:
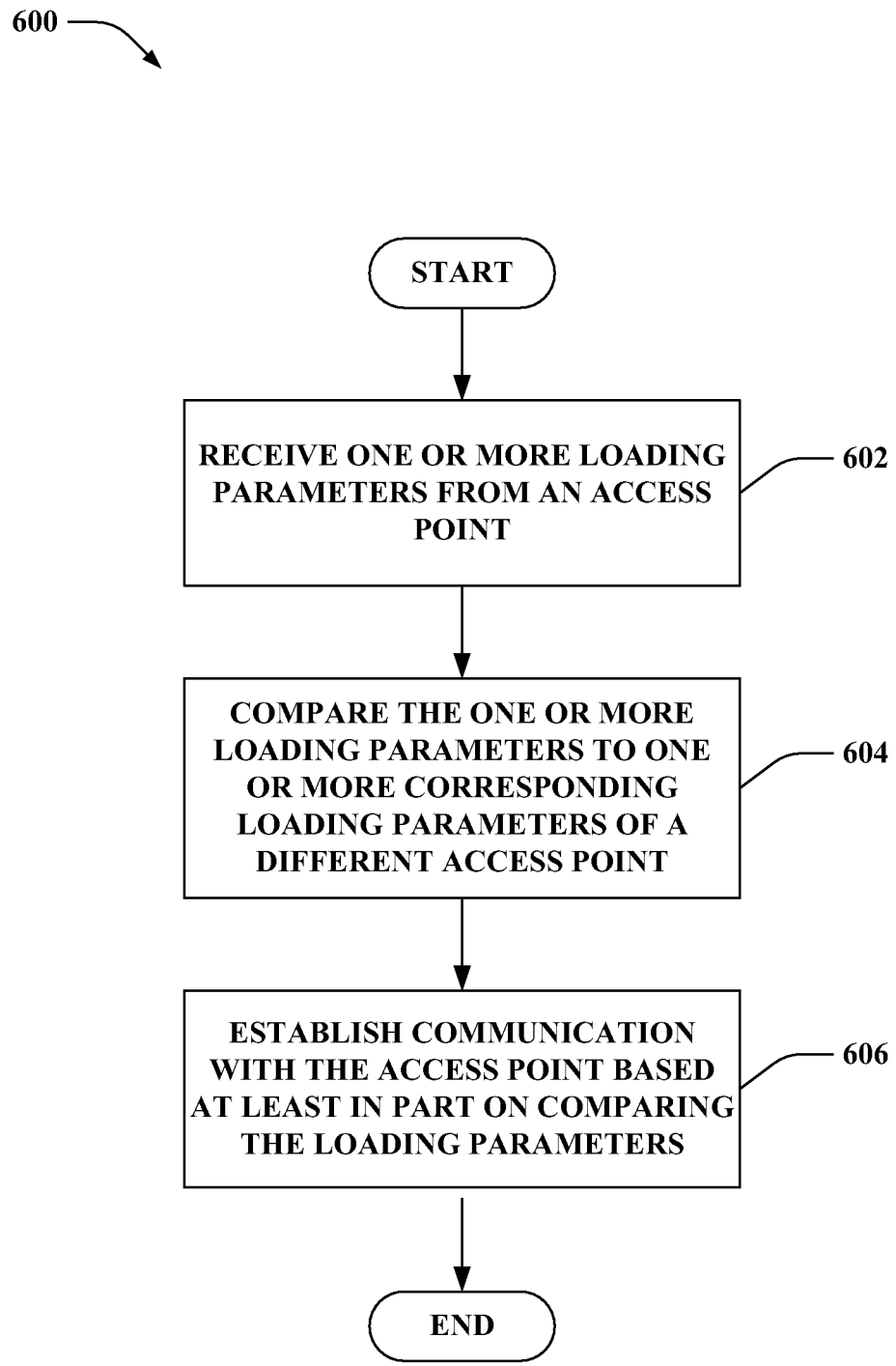
FIG. 6 is an illustration of an example methodology that facilitates cell selection/reselection based on received load parameters.

Referring to FIGS. 5-6, methodologies relating to selecting/reselecting cells according to energy efficiency and/or received loading parameters are illustrated. While, for purposes of simplicity of explanation, the methodologies are shown and described as a series of acts, it is to be understood and appreciated that the methodologies are not limited by the order of acts, as some acts may, in accordance with one or more embodiments, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with one or more embodiments.

Turning to FIG. 5, a methodology 500 that facilitates selecting/reselecting a cell according to an estimated energy efficiency is displayed. At 502, an energy efficiency of an access point is estimated. In an embodiment, a measure of energy efficiency is related to a level of a pathloss measure. Additionally, or alternatively, the energy efficiency can be related to a level of an interference measure. According to an example, the level of pathloss can be estimated based at least in part on a power used by the access point to transmit a signal and the received signal strength. In another example, the level of interference can be measured as a total power received minus a signal power of the access point. It will be appreciated that additional computations or estimates can be utilized to determine the pathloss and/or level of interference. Furthermore, the energy efficiency estimation, as described herein, can be related to additional parameters as well. At 504, the energy efficiency of the access point is compared to an energy efficiency related to a different access point. In one example, the different access point can be a current access point such that the energy efficiencies are compared to determine whether to reselect from a cell of the current access point to a cell of the access point. At 506, communication is established with the access point based at least in part on comparing energy efficiencies. Thus, this can be an initial cell selection and/or reselection, as described. Furthermore, estimated energy efficiencies can be weighted depending on access point type, as described, such that smaller scale access points can be preferred to a certain differential to prevent overloading area macrocell access points.

Turning to FIG. 6, illustrated is a methodology 600 that selects/reselects an access point based at least in part on received loading parameters. At 602, one or more loading parameters are received from an access point. As described, the loading parameters can relate to loading conditions on a cell or related access point, such as a number of devices currently connected, a residual capacity, an associated interference level, etc. The loading parameters can be received in a pilot or other signal transmitted by the access point, from one or more network components, a mobile device, and/or the like. At 604, the one or more loading parameters can be compared to one or more corresponding loading parameters of a different access point. As described, the different access point can be a current access point such that the access point from which the loading parameters are received is evaluated for cell reselection. At 606, communication can be established with the access point based at least in part on comparing the loading parameters. As described, this can relate to establishing initial communications and/or cell reselection.

It will be appreciated that, in accordance with one or more aspects described herein, inferences can be made regarding weighing energy efficiency calculations for different access points (e.g., based on type), as described. As used herein, the term to "infer" or "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. In one example, inferences can additionally be made in evaluating loading parameters (e.g., inferring capacity for an access point to evaluate a current number of connected devices).

Figure 7:
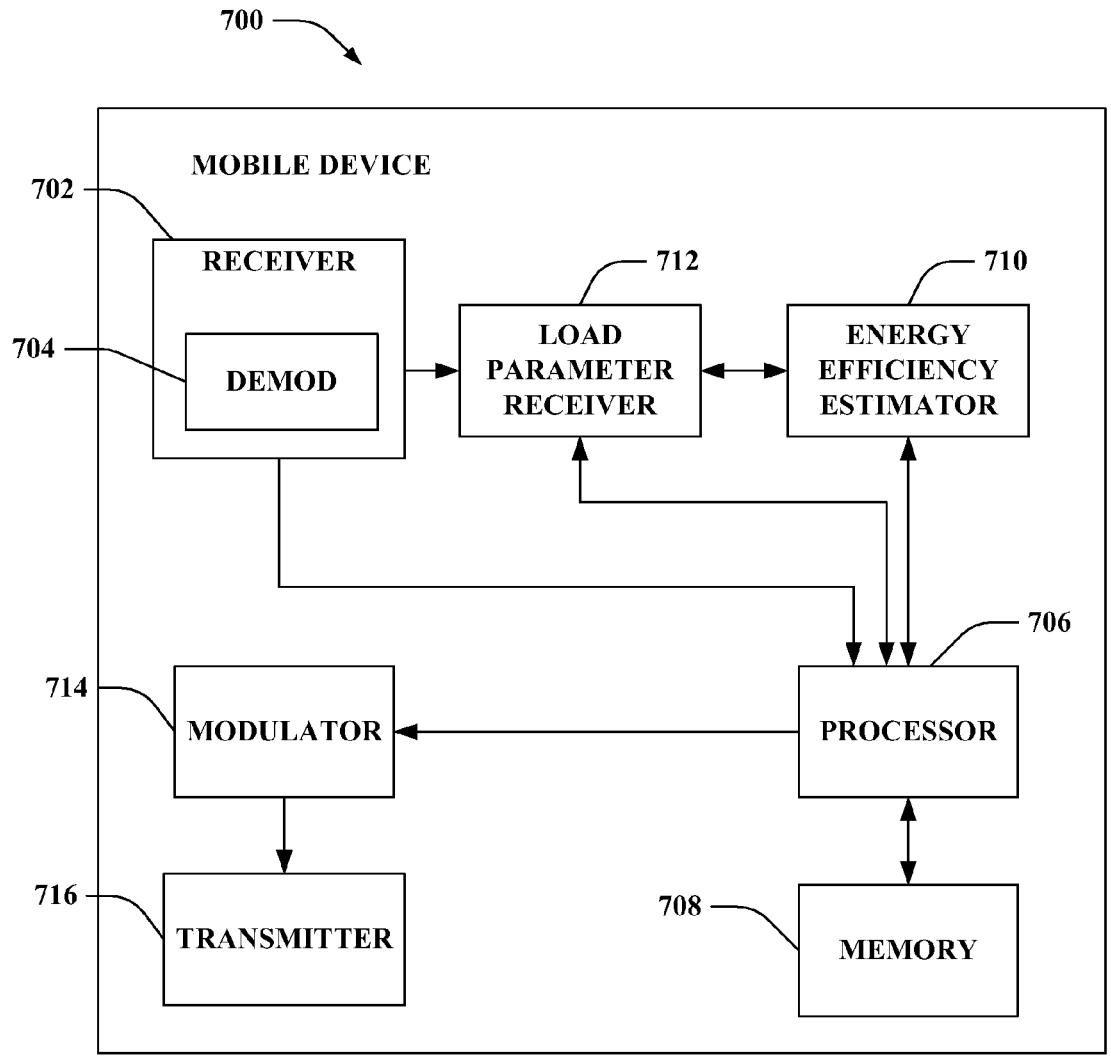
FIG. 7 is an illustration of an example mobile device that facilitates determining a cell or related apparatus for selection/reselection.

FIG. 7 is an illustration of a mobile device 700 that facilitates cell selection/reselection based at least in part on an estimated energy efficiency and/or received load parameters. Mobile device 700 comprises a receiver 702 that receives a signal from, for instance, a receive antenna (not shown), performs typical actions on (e.g., filters, amplifies, downconverts, etc.) the received signal, and digitizes the conditioned signal to obtain samples. Receiver 702 can comprise a demodulator 704 that can demodulate received symbols and provide them to a processor 706 for channel estimation. Processor 706 can be a processor dedicated to analyzing information received by receiver 702 and/or generating information for transmission by a transmitter 716, a processor that controls one or more components of mobile device 700, and/or a processor that both analyzes information received by receiver 702, generates information for transmission by transmitter 716, and controls one or more components of mobile device 700.

Mobile device 700 can additionally comprise memory 708 that is operatively coupled to processor 706 and that can store data to be transmitted, received data, information related to available channels, data associated with analyzed signal and/or interference strength, information related to an assigned channel, power, rate, or the like, and any other suitable information for estimating a channel and communicating via the channel. Memory 708 can additionally store protocols and/or algorithms associated with estimating and/or utilizing a channel (e.g., performance based, capacity based, etc.).

It will be appreciated that the data store (e.g., memory 708) described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable PROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory 708 of the subject systems and methods is intended to comprise, without being limited to, these and any other suitable types of memory.

Processor 706 can further be operatively coupled to an energy efficiency estimator 710 that can calculate energy efficiency for one or more access points as described herein and a load parameter receiver 712 that can receive one or more load parameters from the access points. In particular, the energy efficiency estimator 710 can evaluate pathloss and/or interference levels related to one or more access points and accordingly generate a related energy efficiency estimation, as described above. The processor 706 can utilize the energy efficiency estimation to select or reselect one or more cells (or related access points) to handle subsequent communications. In addition, the load parameter receiver 712 can obtain one or more load parameters related to loading conditions on the one or more access points. The load parameters, for example, can be received from the access point or a disparate network component, mobile device, etc. The processor 706 can additionally or alternatively consider the load parameters in selecting or reselecting one or more access points, as described. Mobile device 700 still further comprises a modulator 714 and transmitter 716 that respectively modulate and transmit signals to, for instance, a base station, another mobile device, etc. Although depicted as being separate from the processor 706, it is to be appreciated that the energy efficiency estimator 710, load parameter receiver 712, demodulator 704, and/or modulator 714 can be part of the processor 706 or multiple processors (not shown).

Figure 8:
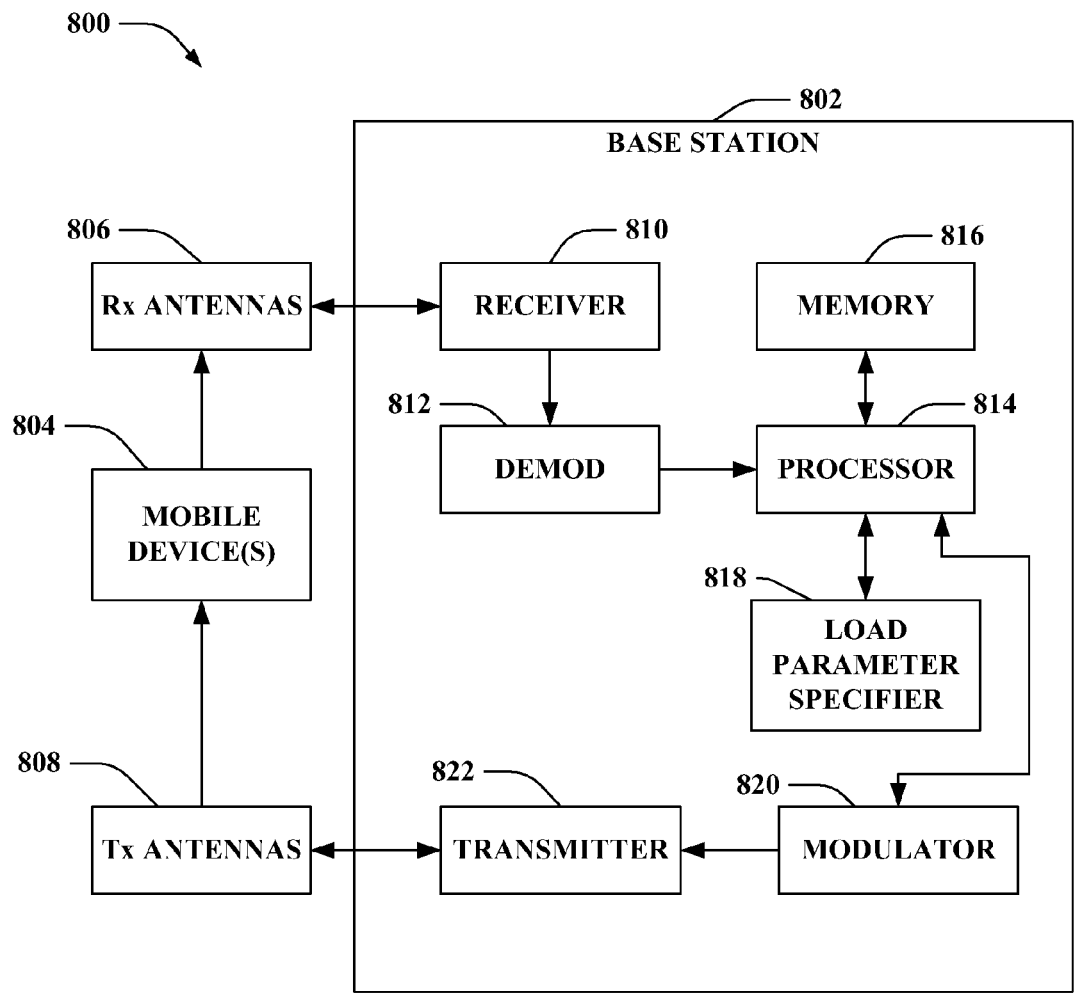
FIG. 8 is an illustration of an example system that transmits load parameters to one or more devices.

FIG. 8 is an illustration of a system 800 that facilitates transmitting load parameters to one or more devices. The system 800 comprises a base station 802 (e.g., access point, . . . ) with a receiver 810 that receives signal(s) from one or more mobile devices 804 through a plurality of receive antennas 806, and a transmitter 822 that transmits to the one or more mobile devices 804 through a transmit antenna 808. Receiver 810 can receive information from receive antennas 806 and is operatively associated with a demodulator 812 that demodulates received information. Demodulated symbols are analyzed by a processor 814 that can be similar to the processor described above with regard to FIG. 7, and which is coupled to a memory 816 that stores information related to estimating a signal (e.g., pilot) strength and/or interference strength, data to be transmitted to or received from mobile device(s) 804 (or a disparate base station (not shown)), and/or any other suitable information related to performing the various actions and functions set forth herein. Furthermore, the modulator 820 can similarly modulate data into signals for transmission over the transmitter 822 to the one or more mobile devices 804. Processor 814 is further coupled to a load parameter specifier 818 that can generate load parameters for transmitting to one or more mobile devices 804.

According to an example, the load parameter specifier 818 can generate the parameters based at least in part on sensed or received loading conditions related to the base station 802. In one example, the parameters can include a number of mobile devices 804 currently served by the base station 802, a number of devices that can be served by the base station 802, a residual capacity of the base station 802, interference experienced at the base station 802, and/or the like, as described. The base station 802 can transmit the load parameters to the one or more mobile devices 804 to allow the mobile devices 804 to consider the parameters in determining access points for selection/reselection. Furthermore, although depicted as being separate from the processor 814, it is to be appreciated that the load parameter specifier 818, demodulator 812, and/or modulator 820 can be part of the processor 814 or multiple processors (not shown).

Figure 9:
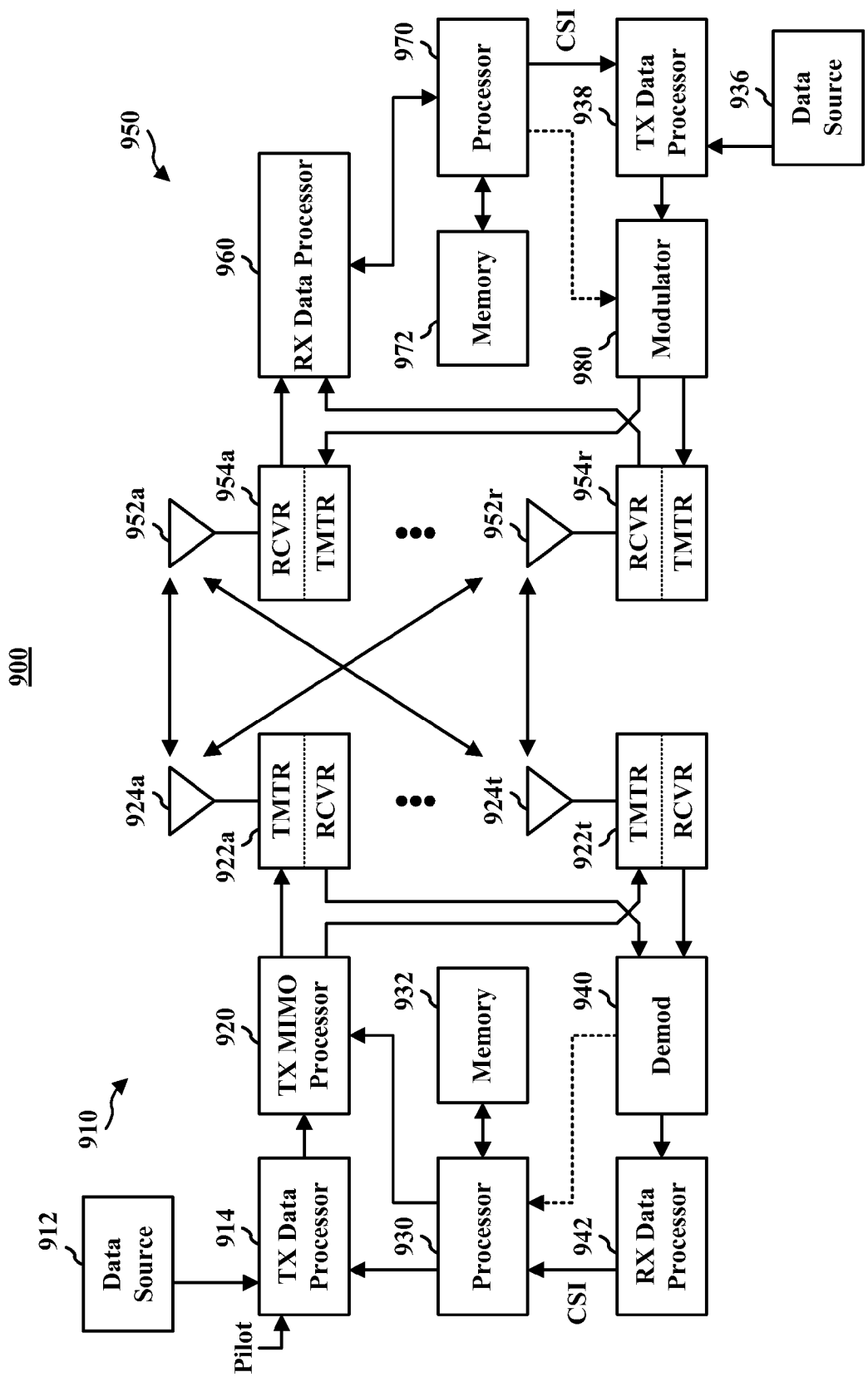
FIG. 9 is an illustration of an example wireless network environment that can be employed in conjunction with the various systems and methods described herein.

FIG. 9 shows an example wireless communication system 900. The wireless communication system 900 depicts one base station 910 and one mobile device 950 for sake of brevity. However, it is to be appreciated that system 900 can include more than one base station and/or more than one mobile device, wherein additional base stations and/or mobile devices can be substantially similar or different from example base station 910 and mobile device 950 described below. In addition, it is to be appreciated that base station 910 and/or mobile device 950 can employ the systems (FIGS. 1-4 and 7-8) and/or methods (FIGS. 5-6) described herein to facilitate wireless communication there between.

At base station 910, traffic data for a number of data streams is provided from a data source 912 to a transmit (TX) data processor 914. According to an example, each data stream can be transmitted over a respective antenna. TX data processor 914 formats, codes, and interleaves the traffic data stream based on a particular coding scheme selected for that data stream to provide coded data.

The coded data for each data stream can be multiplexed with pilot data using orthogonal frequency division multiplexing (OFDM) techniques. Additionally or alternatively, the pilot symbols can be frequency division multiplexed (FDM), time division multiplexed (TDM), or code division multiplexed (CDM). The pilot data is typically a known data pattern that is processed in a known manner and can be used at mobile device 950 to estimate channel response. The multiplexed pilot and coded data for each data stream can be modulated (e.g., symbol mapped) based on a particular modulation scheme (e.g., binary phase-shift keying (BPSK), quadrature phase-shift keying (QPSK), M-phase-shift keying (M-PSK), M-quadrature amplitude modulation (M-QAM), etc.) selected for that data stream to provide modulation symbols. The data rate, coding, and modulation for each data stream can be determined by instructions performed or provided by processor 930.

The modulation symbols for the data streams can be provided to a TX MIMO processor 920, which can further process the modulation symbols (e.g., for OFDM). TX MIMO processor 920 then provides $N_T$ modulation symbol streams to $N_T$ transmitters (TMTR) 922a through 922t. In various embodiments, TX MIMO processor 920 applies beamforming weights to the symbols of the data streams and to the antenna from which the symbol is being transmitted.

Each transmitter 922 receives and processes a respective symbol stream to provide one or more analog signals, and further conditions (e.g., amplifies, filters, and upconverts) the analog signals to provide a modulated signal suitable for transmission over the MIMO channel. Further, $N_T$ modulated signals from transmitters 922a through 922t are transmitted from $N_T$ antennas 924a through 924t, respectively.

At mobile device 950, the transmitted modulated signals are received by $N_R$ antennas 952a through 952r and the received signal from each antenna 952 is provided to a respective receiver (RCVR) 954a through 954r. Each receiver 954 conditions (e.g., filters, amplifies, and downconverts) a respective signal, digitizes the conditioned signal to provide samples, and further processes the samples to provide a corresponding "received" symbol stream.

An RX data processor 960 can receive and process the $N_R$ received symbol streams from $N_R$ receivers 954 based on a particular receiver processing technique to provide $N_T$ "detected" symbol streams. RX data processor 960 can demodulate, deinterleave, and decode each detected symbol stream to recover the traffic data for the data stream. The processing by RX data processor 960 is complementary to that performed by TX MIMO processor 920 and TX data processor 914 at base station 910.

A processor 970 can periodically determine which precoding matrix to utilize as discussed above. Further, processor 970 can formulate a reverse link message comprising a matrix index portion and a rank value portion.

The reverse link message can comprise various types of information regarding the communication link and/or the received data stream. The reverse link message can be processed by a TX data processor 938, which also receives traffic data for a number of data streams from a data source 936, modulated by a modulator 980, conditioned by transmitters 954a through 954r, and transmitted back to base station 910.

At base station 910, the modulated signals from mobile device 950 are received by antennas 924, conditioned by receivers 922, demodulated by a demodulator 940, and processed by a RX data processor 942 to extract the reverse link message transmitted by mobile device 950. Further, processor 930 can process the extracted message to determine which precoding matrix to use for determining the beamforming weights.

Processors 930 and 970 can direct (e.g., control, coordinate, manage, etc.) operation at base station 910 and mobile device 950, respectively. Respective processors 930 and 970 can be associated with memory 932 and 972 that store program codes and data. Processors 930 and 970 can also perform computations to derive frequency and impulse response estimates for the uplink and downlink, respectively.

It is to be understood that the embodiments described herein can be implemented in hardware, software, firmware, middleware, microcode, or any combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof.

When the embodiments are implemented in software, firmware, middleware or microcode, program code or code segments, they can be stored in a machine-readable medium, such as a storage component. A code segment can represent a procedure, a function, a subprogram, a program, a routine, a subroutine, a module, a software package, a class, or any combination of instructions, data structures, or program statements. A code segment can be coupled to another code segment or a hardware circuit by passing and/or receiving information, data, arguments, parameters, or memory contents. Information, arguments, parameters, data, etc. can be passed, forwarded, or transmitted using any suitable means including memory sharing, message passing, token passing, network transmission, etc.

For a software implementation, the techniques described herein can be implemented with modules (e.g., procedures, functions, and so on) that perform the functions described herein. The software codes can be stored in memory units and executed by processors. The memory unit can be implemented within the processor or external to the processor, in which case it can be communicatively coupled to the processor via various means as is known in the art.

Figure 10:
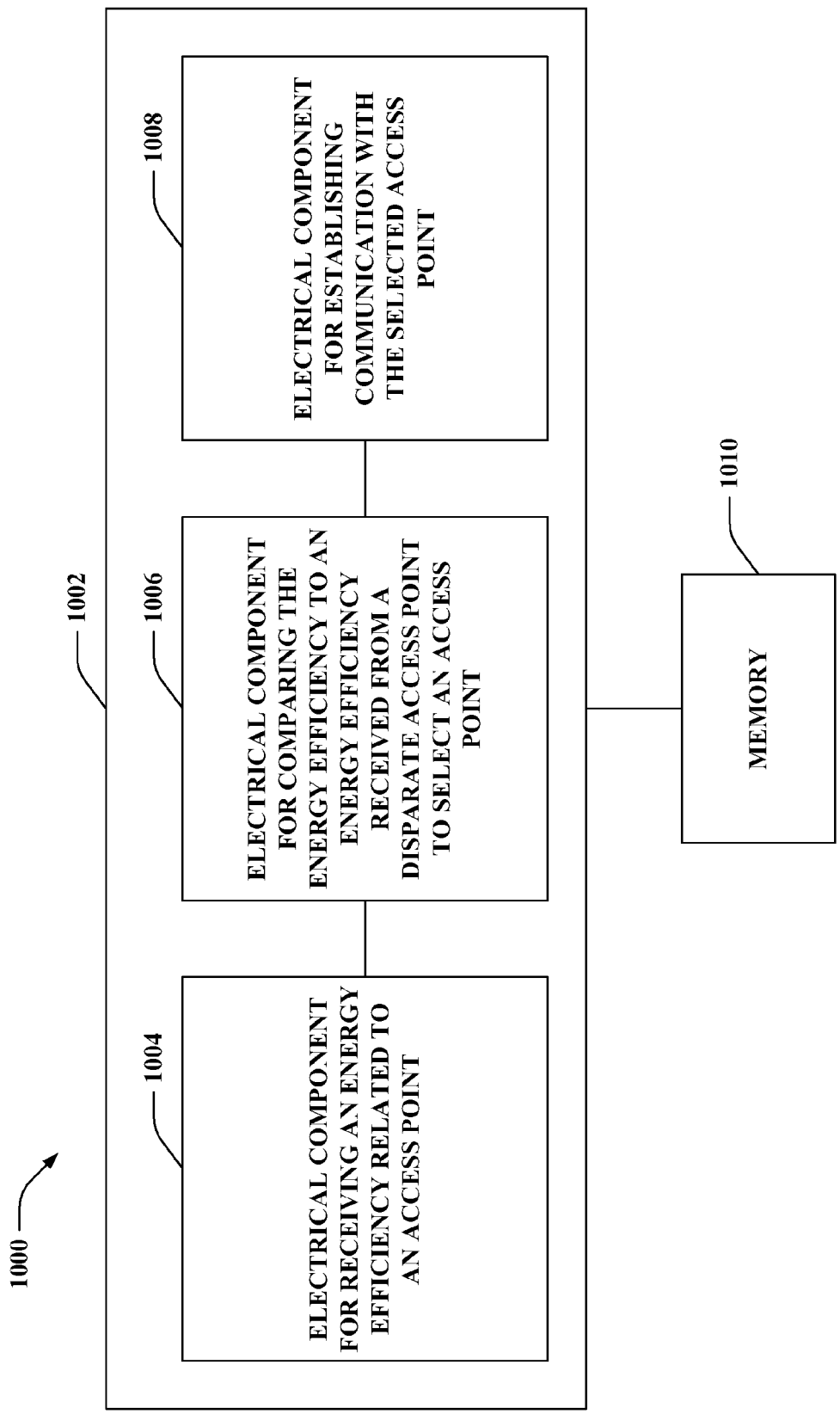
FIG. 10 is an illustration of an example system that establishes communications with one or more access points based at least in part on an estimated energy efficiency.

With reference to FIG. 10, illustrated is a system 1000 that establishes communications with one or more access points based at least in part on a received energy efficiency related to the access points. For example, system 1000 can reside at least partially within a base station, mobile device, etc. It is to be appreciated that system 1000 is represented as including functional blocks, which can be functional blocks that represent functions implemented by a processor, software, or combination thereof (e.g., firmware). System 1000 includes a logical grouping 1002 of electrical components that can act in conjunction. For instance, logical grouping 1002 can include an electrical component for receiving an energy efficiency related to an access point 1004. For example, the energy efficiency can be received from a component that estimates the energy efficiency (not shown). In one example, the energy efficiency can be calculated based on an estimated pathloss and/or a level of interference related to the access point, as described. Further, logical grouping 1002 can comprise an electrical component for comparing the energy efficiency to an energy efficiency received from a disparate access point to select an access point 1006. As described, the access point can be selected for initial communication establishment, as part of a cell reselection procedure, and/or the like. To this end, logical grouping 1002 can include an electrical component for establishing communication with the selected access point 1008. Additionally, system 1000 can include a memory 1010 that retains instructions for executing functions associated with electrical components 1004, 1006, and 1008. While shown as being external to memory 1010, it is to be understood that one or more of electrical components 1004, 1006, and 1008 can exist within memory 1010.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Additionally, at least one processor may comprise one or more modules operable to perform one or more of the steps and/or actions described above.

Further, the steps and/or actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or actions of a method or algorithm may reside as one or any combination or set of codes and/or instructions on a machine readable medium and/or computer readable medium, which may be incorporated into a computer program product.

In one or more aspects, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection may be termed a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs usually reproduce data optically with lasers. Combinations of the above should also be included within the scope of computer-readable media.

What is claimed is:

1. A method for evaluating an access point for initial communication establishment or reselection thereto, comprising:
   estimating a first energy efficiency related to a pathloss and/or a level of interference associated with a first access point, wherein the pathloss relates to a reduction in power of a signal between a transmitter and a receiver;
   comparing the first energy efficiency to a second energy efficiency of a second access point to determine which one of the first energy efficiency or the second energy efficiency is higher; and
   at least partly in response to the determination, establishing communication with the first access point if the first energy efficiency is higher than the second energy efficiency or establishing communication with the second access point if the second energy efficiency is higher than the first energy efficiency;
   wherein the first energy efficiency or the second energy efficiency are computed based at least partly on a symbol rate, a total received power, a received signal power, and the pathloss.

2. The method of claim 1, further comprising receiving one or more load parameters related to resource usage and capacity of the access point.

3. The method of claim 2, wherein establishing communication with the first access point or the second access point is further based on comparing the one or more load parameters to one or more load parameters related to the second access point.

4. The method of claim 2, wherein the one or more load parameters includes a number of devices currently communicating with the first access point and/or with the second access point.

5. The method of claim 1, wherein the level of interference is determined as a power of a signal received from the first access point or the second access point subtracted from a total received power.

6. The method of claim 1, wherein the pathloss is estimated based at least in part on a transmit power of the first access point or the second access point and a received power measurement related to the first access point or the second access point.

7. The method of claim 1, wherein establishing communication with the first access point or the second access point is performed as part of a cell reselection from a current access point, wherein one of the first access point or the second access point is the current access point.

8. The method of claim 7, further comprising initiating the cell reselection based at least in part on comparing the first energy efficiency or the second energy efficiency with a current energy efficiency related to the current access point.

9. The method of claim 1, wherein the first energy efficiency and the second energy efficiency are computed according to the following formula:

$$E_{b,tx} \approx (\log 2/B)(Y-C)/h$$

wherein $E_{b,tx}$ is the energy efficiency of an access point to be computed, B is the symbol rate, Y is the total received power, C is the received signal power, and h is the pathloss.

10. A wireless communications apparatus, comprising:
at least one processor configured to:
receive a first energy efficiency related to a pathloss or a level of interference associated with a first access point, wherein the pathloss relates to a reduction in power of a signal between a transmitter and a receiver;
receive a second energy efficiency related to a pathloss or a level of interference associated with a second access point;
compare the first energy efficiency to the second energy efficiency to select one of the first access point or the second access point for receiving wireless access services based at least in part on which one of the first access point or the second access point is associated with better energy efficiency; and
establish communication with the selected one of the access points; and
a memory coupled to the at least one processor;
wherein the first energy efficiency or the second energy efficiency are computed based at least partly on a symbol rate, a total received power, a received signal power, and the pathloss.

11. The wireless communications apparatus of claim 10, wherein the first energy efficiency and the second energy efficiency are computed according to the following formula:

$$E_{b,tx} \approx (\log 2/B)(Y-C)/h$$

wherein $E_{b,tx}$ is the energy efficiency of an access point to be computed, B is the symbol rate, Y is the total received power, C is the received signal power, and h is the pathloss.

12. A wireless communications apparatus that facilitates analyzing an access point for selection or reselection thereto, comprising:
means for receiving a first energy efficiency related to a first access point;
means for comparing the first energy efficiency to a second energy efficiency received from a second access point to select one of the first access point or the second access point based at least in part on which one has better energy efficiency; and
means for establishing communication with the selected one of the access points;
wherein the first energy efficiency and the second energy efficiency are computed based at least partly on a symbol rate, a total received power, a received signal power, and the pathloss.

13. The wireless communications apparatus of claim 12, wherein the first energy efficiency and the second energy efficiency are computed according to the following formula:

$$E_{b,tx} \approx (\log 2/B)(Y-C)/h$$

wherein $E_{b,tx}$ is the energy efficiency of an access point to be computed, B is the symbol rate, Y is the total received power, C is the received signal power, and h is the pathloss.

14. An apparatus comprising:
at least one processor configured to execute code stored on a non-transitory computer-readable medium; and
the non-transitory computer-readable medium comprising:
code for causing the at least one processor to estimate a first energy efficiency related to a pathloss and/or a level of interference associated with a first access point, wherein the pathloss relates to a reduction in power of a signal between a transmitter and a receiver;
code for causing the at least one processor to compare the first energy efficiency to a second energy efficiency of a second access point; and
code for causing the at least one processor to establish communication with one of the first access point or the second access point based at least in part on which one of the first access point or the second access point has better energy efficiency;
wherein the first energy efficiency or the second energy efficiency are computed based at least partly on a symbol rate, a total received power, a received signal power, and the pathloss.

15. The apparatus of claim 14, wherein the first energy efficiency and the second energy efficiency are computed according to the following formula:

$$E_{b,tx} \approx (\log 2/B)(Y-C)/h$$

wherein $E_{b,tx}$ is the energy efficiency of an access point to be computed, B is the symbol rate, Y is the total received power, C is the received signal power, and h is the pathloss.

16. An apparatus, comprising:
an energy efficiency estimator that is configured to calculate a first energy efficiency related to a first access point; and
a cell selector that is configured to compare the first energy efficiency with a second energy efficiency related to a second access point and is configured to select one of the first access point or the second access point for receiving wireless access services based at least on which one has better energy efficiency;
wherein the first energy efficiency or the second energy efficiency are computed based at least partly on a symbol rate, a total received power, a received signal power, and the pathloss.

17. The apparatus of claim 16, further comprising a pathloss evaluator that is configured to estimate a pathloss related to the first access point or the second access point based at least in part on a transmit power of the first access point or the second access point for a signal and a power received from the signal.

18. The apparatus of claim 17, wherein the energy efficiency estimator utilizes the pathloss to calculate the first energy efficiency or the second energy efficiency.

19. The apparatus of claim 16, further comprising an interference determiner that calculates a level of interference related to communicating with the first access point or the second access point as a power of a signal received from the first access point or the second access point subtracted from a total received power.

20. The apparatus of claim 19, wherein the energy efficiency estimator calculates the energy efficiency based at least in part on the level of interference.

21. The apparatus of claim 16, further comprising a loading parameter evaluator that receives one or more load parameters from the first access point or the second access point.

22. The apparatus of claim 21, wherein the cell selector further compares the load parameters to one or more load parameters related to the second access point and selects the first access point or the second access point further based at least in part on comparing the load parameters.

23. The apparatus of claim 21, wherein the one or more load parameters includes a residual capacity of the first access point or the second access point.

24. The apparatus of claim 16, wherein the cell selector selects the first access point or the second access point as part of a cell reselection from a current access point, wherein one of the first access point or the second access point is the current access point.

25. The apparatus of claim 24, the cell selector initiates the cell reselection based at least in part on comparing the first energy efficiency or the second energy efficiency with a current energy efficiency related to the current access point.

26. The apparatus of claim 16, wherein the first energy efficiency and the second energy efficiency are computed according to the following formula:

$$E_{b,tx} \approx (\log 2/B)(Y-C)/h$$

wherein $E_{b,tx}$ is the energy efficiency of an access point to be computed, B is the symbol rate, Y is the total received power, C is the received signal power, and h is the pathloss.

27. A method of selecting an access point, the method comprising:
    identifying a plurality of candidate access points for communication with a terminal, at least two of the plurality of candidate access points having different levels of at least one communication parameter, wherein the at least one communication parameter includes a measure of pathloss, wherein the pathloss relates to a reduction in power of a signal between a transmitter and a receiver; and
    selecting a candidate access point from among the plurality of candidate access points when the candidate access point has at least a lower level of the at least one communication parameter than a highest level of the at least one communication parameter among the plurality of access points;
    wherein the pathloss for a candidate access point is computed based at least partly on a signal power from the candidate access point and an equivalent isotropically radiated power.

28. The method of claim 27, wherein the at least one communication parameter further includes a load parameter.

29. The method of claim 28, wherein the load parameter further includes a number of devices in communication with an access point.

30. The method of claim 27, wherein the at least one communication parameter further includes an energy efficiency, wherein the selected candidate access point has a higher level of energy efficiency than a lowest level of the energy efficiencies of the plurality of access points.

31. The method of claim 27, wherein the at least one communication parameter further includes a measure of interference.

32. The method of claim 27, wherein the pathloss for a candidate access point i is computed according to the following formula:

$$h = C_i / \text{EIRP}_i$$

wherein h is the pathloss, $C_i$ is a signal power from the candidate access point i, and $\text{EIRP}_i$ is the equivalent isotropically radiated power related to the candidate access point i.

* * * * *